(12) United States Patent
Hatch et al.

(10) Patent No.: US 7,463,158 B2
(45) Date of Patent: Dec. 9, 2008

(54) ACOUSTIC PARTICLE ALARM INCLUDING PARTICLE SENSOR

(75) Inventors: Robert K. Hatch, San Diego, CA (US); William D. Squire, San Diego, CA (US); Harper J. Whitehouse, San Diego, CA (US)

(73) Assignee: Linear Measurements, Inc., San Diego, CA (US)

( * ) Notice: Subject to any disclaimer, the term of this patent is extended or adjusted under 35 U.S.C. 154(b) by 7 days.

(21) Appl. No.: 11/253,364

(22) Filed: Oct. 19, 2005

(65) Prior Publication Data
US 2008/0084321 A1 Apr. 10, 2008

(51) Int. Cl.
*G08B 21/00* (2006.01)

(52) U.S. Cl. .................. 340/627; 73/53.01; 73/861.18; 73/861.21; 702/128; 702/129

(58) Field of Classification Search .................. 340/627; 73/53.01, 53.07, 861.04, 861.07, 861.18, 73/861.21, 861.73, 865.5, 375.5, 375.6, 861.018; 702/53, 128, 129
See application file for complete search history.

(56) References Cited

U.S. PATENT DOCUMENTS

| | | | | |
|---|---|---|---|---|
| 3,765,771 A | * | 10/1973 | Shaw | ........................... 377/10 |
| 4,240,287 A | * | 12/1980 | Mast et al. | .................. 73/61.75 |
| 5,257,530 A | | 11/1993 | Beattie et al. | |
| 5,969,236 A | * | 10/1999 | Hirota et al. | ............... 73/61.75 |
| 6,561,005 B2 | | 5/2003 | Muller et al. | |
| 2005/0175508 A1 | * | 8/2005 | Hill | .............................. 422/73 |

* cited by examiner

*Primary Examiner*—Jeff Hofsass
*Assistant Examiner*—Hongmin Fan
(74) *Attorney, Agent, or Firm*—Peter K. Hahn; Luce, Forward, Hamilton & Scripps (57) ABSTRACT

The present invention provides an acoustic particle alarm comprising a particle sensor for indicating the concentration of particles exceeding a specified size and specified concentration, for particles entrained in a fluid flow impinging on a front face of the sensor, and a nozzle for directing the fluid flow such that the particles impact the sensor in a direction substantially normal to the front face of the sensor. Each particle impacting the front face of the sensor causes a response in an output of the sensor with amplitude that is monotonic in the momentum of the impinging particle.

17 Claims, 3 Drawing Sheets

ACOUSTIC PARTICLE ALARM INCLUDING PARTICLE SENSOR

FIELD OF THE INVENTION

The present invention is directed to an acoustic particle alarm, and more particularly, to an acoustic particle alarm including a particle sensor for indicating the concentration of particles exceeding a specified size and concentration entrained in a fluid flow impinging the particle sensor.

BACKGROUND OF THE INVENTION

Solid particles entrained in a moving fluid within a conduit can be monitored using acoustic means. Specifically, the sonic and ultrasonic signatures caused when the particles impact the wall of the conduit can be detected due to the transfer of momentum to the surrounding conduit. A sensor such as an acoustic transducer can be inserted either directly into the fluid flow or attached to the surrounding conduit. The fluid can be either a gas such as air or a viscous fluid such and oil or water. Particle impacts occur when the motion of the fluid is changed by a modification of the flow such as a by a bend in the conduit.

U.S. Pat. No. 5,969,236 discloses a particle sensor comprising a sensor element including a vibrating section having a mass that is sensitive to the collision of solid particles contained in a fluid and a detecting section for detecting the vibration of the vibrating section caused by the collision and converting the vibration to electric signals. The particle sensor also includes through holes that are formed in the sensor element in the vicinity of the vibrating section, such that the fluid entering the particle sensor from an inlet nozzle collides with the sensor element, passes through the through holes and leaves the particle sensor from the outlet nozzle. The particle sensor is adapted to measure the sizes and particle size distribution of particles contained in the fluid.

The particle sensor described in U.S. Pat. No. 5,969,236 suffers from a number of drawbacks. One drawback is that means are not provided to ensure that the particles impact the particle sensor in a direction substantially normal to the front face of the sensor rather than following the fluid flow away from the sensor. A further drawback is that the electrical signal produced by impinging particles is not necessarily a monotonic function of the momentum of the impinging particles. An additional drawback is that this reference does not provide an indicator for indicating when integrated particle impacts are greater than an acceptable threshold revel.

In view of the above, there exists a need for an acoustic particle alarm having a particle sensor comprising a monitoring flow cell including an acoustic particle sensor that produces an output signal in response to particle (or contaminant) impacts in a fluid flow that is impinging on the acoustic sensor.

There also exists a need for an acoustic particle alarm having a particle sensor comprising a monitoring flow cell including an acoustic sensor that produces an output signal in response to particle impacts in a fluid flow that is impinging on the acoustic sensor, wherein the acoustic sensor is isolated from the flow cell to reduce the acoustic coupling between the sensor and the other elements of the flow cell.

There further exists a need for a method of establishing the fluid flow onto an acoustic sensor such that particulate matter in fluid flow impacts a face of the acoustic sensor in a direction substantially normal to the face of the acoustic sensor.

Additionally, there exists a need for a method of establishing fluid flow onto an acoustic sensor such that particulate matter in fluid flow impacts a face of the acoustic sensor with as much velocity as is permitted by flow noise.

There also exists a need for a method of establishing fluid flow onto an acoustic sensor such that particulate matter in fluid flow impacts a face of the acoustic sensor rather than following the fluid flow away from the sensor.

There further exists a need for a method of establishing fluid flow onto an acoustic sensor at a preferred flow velocity.

Additionally, there exists a need for a method of establishing fluid flow onto an acoustic sensor, wherein the particle impact signal is separable from the flow noise.

There also exists a need for a method of establishing fluid flow onto an acoustic sensor, wherein the amplitude of the electrical signal produced by impinging particles is monotonic in the momentum of the impinging particles.

There further exists a need for a method of establishing fluid flow onto an acoustic sensor and measuring the integrated contribution of impinging particles on the acoustic sensor.

Additionally, there exists a need for an acoustic particle alarm including a particle sensor that produces an output signal in response to particle impacts in a fluid flow and an indicator for indicating when the integrated particle impacts are greater than an acceptable threshold level.

SUMMARY OF THE INVENTION

In view of the foregoing, it is an object of the present invention to provide an acoustic particle alarm having a particle sensor comprising a monitoring flow cell including an acoustic particle sensor that produces an output signal in response to particle (or contaminant) impacts in a fluid flow that is impinging on the acoustic sensor.

It is a further object of the invention to provide an acoustic particle alarm comprising a monitoring flow cell including an acoustic sensor that produces an output signal in response to particle impacts in a fluid flow that is impinging on the acoustic sensor, wherein the acoustic sensor is isolated from the flow cell to reduce the acoustic coupling between the acoustic sensor and the other elements of the flow cell.

It is another object of the invention to provide a method of establishing the fluid flow onto an acoustic sensor such that particulate matter in fluid flow impacts a face of the acoustic sensor in a direction substantially normal to the face of the acoustic sensor.

It is a further object of the invention to provide a method of establishing fluid flow onto an acoustic sensor such that particulate matter in fluid flow impacts a face of the acoustic sensor with as much velocity as is permitted by flow noise.

It is an additional object of the invention to provide a method of establishing fluid flow onto an acoustic sensor such that particulate matter in fluid flow impacts a face of the acoustic sensor rather than following the fluid flow away from the sensor.

It is another object of the invention to provide a method of establishing fluid flow onto an acoustic sensor at a preferred flow velocity.

It is a further object of the invention to provide a method of establishing fluid flow onto an acoustic sensor, wherein the particle impact signal is separable from the flow noise.

It is an additional object of the invention to provide a method of establishing fluid flow onto an acoustic sensor, wherein the amplitude of the electrical signal produced by impinging particles is monotonic in the momentum of the impinging particles.

It is another object of the invention to provide a method of establishing fluid flow onto an acoustic sensor that produces an output signal in response to the integrated contribution of impinging particles on the acoustic sensor.

It is yet another object of the invention to provide an acoustic particle alarm including an acoustic sensor that produces an output signal in response to particle impacts in a fluid flow and an indicator for indicating when the integrated particle impacts are greater than an acceptable threshold level.

One aspect of the present invention involves an acoustic particle alarm comprising a particle sensor that produces an output signal in response to the momentum of particles entrained in a fluid flow impinging on a front face of the sensor and a nozzle for directing the fluid flow such that the particles impact the sensor in a direction substantially normal to the front face of the sensor. Each particle impacting the front face of the sensor causes a response in an output of the sensor that is monotonic in the momentum of the impinging particle. The sensor may comprise a piezoelectric or ferroelectric acoustic transducer that produces an output signal in response to the momentum of the particles as they impact the diaphragm of the sensor.

According to some embodiments of the invention: (1) the nozzle is releasably attached to a mounting block within a first threaded mounting block opening in one side of the mounting block; (2) the sensor is housed within a sensor housing that is inserted in a second threaded mounting block opening on the opposite side of the mounting block; and (3) the sensor housing is secured within the mounting block opening using a retaining nut that is releasably attached within the second threaded mounting block opening. The sensor housing and retaining nut each include a central aperture that forms a cavity adjacent to the sensor, wherein the cavity is dimensioned to contain electronics for operating the acoustic particle alarm.

According to further embodiments of the invention: (1) the nozzle is releasably attached to a mounting block within a first threaded mounting block opening in one side of the mounting block; and (2) the sensor is housed within an integrated sensor housing and retaining nut that is attached to the mounting block within a second threaded mounting block opening on the opposite side of the mounting block. The integrated sensor housing and retaining nut includes a central aperture that forms a cavity adjacent to the sensor, wherein the cavity is dimensioned to contain electronics for operating the acoustic particle alarm.

According to further embodiments of the invention: (1) the nozzle is permanently attached to a mounting block; and (2) the sensor is housed within an integrated sensor housing and retaining nut that is attached to the mounting block within a second threaded mounting block opening on the opposite side of the mounting block. The integrated sensor housing and retaining nut includes a central aperture that forms a cavity adjacent to the sensor, wherein the cavity is dimensioned to contain electronics for operating the acoustic particle alarm.

Another aspect of the invention involves an acoustic particle alarm comprising a particle sensor that produces an output signal in response to the momentum of particles entrained in a fluid flow impinging on a diaphragm of the sensor, wherein the sensor is disposed within the sensor housing and a nozzle for directing the fluid flow such that a jet of fluid exiting a mouth of the nozzle forms a waist that is located substantially at the diaphragm. The acoustic particle alarm further comprises a mounting block including a detachable sensor housing, wherein a gap is disposed between the sensor housing and the mounting block to reduce the amount of acoustic coupling between the sensor and the mounting block. One or more seals may also be provided between the sensor housing and the mounting block to reduce the amount of acoustic coupling between the sensor and the mounting block.

According to a preferred implementation of the invention: (1) the nozzle includes a mouth that is disposed at a predetermined distance from the diaphragm; (2) the mouth of the nozzle includes a substantially conical bore that causes the fluid exiting the mouth to form a waist; and (3) the predetermined distance is selected such that the waist is substantially disposed at the diaphragm, thereby maximizing the concentration of particles impacting the sensor. The predetermined distance is selected to be greater than a maximum dimension of the largest particle to be passed. Additionally, a minimum inside diameter of the substantially conical bore is greater than the maximum dimension of the largest particle to be passed. The flow velocity of the fluid through the nozzle is selected to be just below the velocity at which flow noise at the predominant frequency of the sensor impact signals is comparable to the electronic noise in the absence of flow.

A further aspect of the invention involves an acoustic particle alarm comprising a particle sensor that measures the integrated contribution of particles within a fluid flow impinging on the sensor, an amplifying circuit for amplifying the signal produced by particle impacts and for attenuating the signal produced by flow noise, a first threshold circuit for determining if an output signal exceeds a predetermined threshold level, an accumulator that integrates the outputs of the threshold circuit and a second threshold circuit that actuates an alarm circuit including an indicator that indicates when the accumulated output signal exceeds the predetermined second threshold level. The amplifying circuit includes a filter that is suitable to pass the signal, but attenuate the noise in bands outside of frequencies occupied by the signal. According to a preferred embodiment, the indicator comprises one or more light emitting diodes.

These and other features and advantages of the present invention will be appreciated from review of the following detailed description of the invention, along with the accompanying figures in which like reference numerals refer to like parts throughout.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Figure 1:
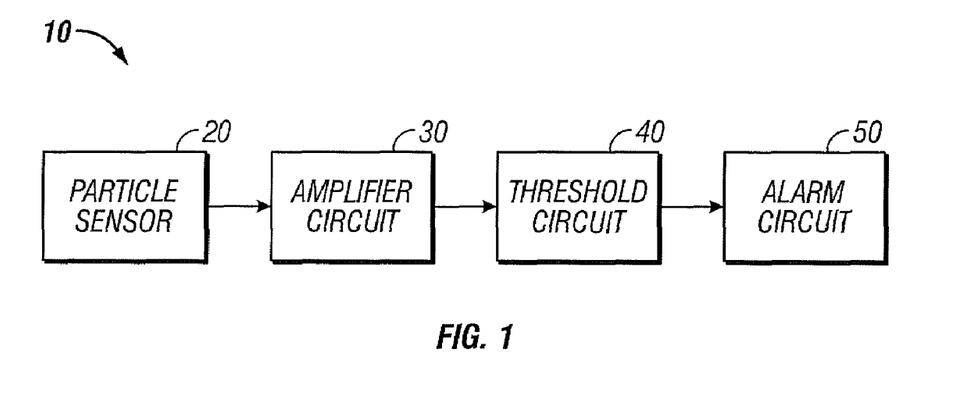
FIG. 1 is a schematic diagram of an acoustic particle alarm according to the principles of the present invention.

Particle impacts occur when the motion of a particle-containing fluid is changed by a modification of the flow, such as an obstruction or a bend in a conduit. The resultant particle impacts may be detected due to the transfer of momentum to an acoustic sensor within the conduit. Referring to FIG. 1, the present invention provides an acoustic particle alarm 10 including a particle sensor 20 that produces an output signal in response to the particles impinging on the sensor. Acoustic particle alarm 10 further comprises: an amplifying circuit 30 for increasing the output signal produced by particle impacts and attenuating the output signal produced by noise; a first threshold circuit 40 for determining if the output signal exceeds a predetermined level; and an alarm circuit 50 comprising an accumulator with a second threshold circuit, including an indicator for indicating when the integrated particle impact is greater than the predetermined second threshold level. The indicator may comprise a comparator and an indicator circuit such as one or more light emitting diode diodes (LEDs).

Figure 2:
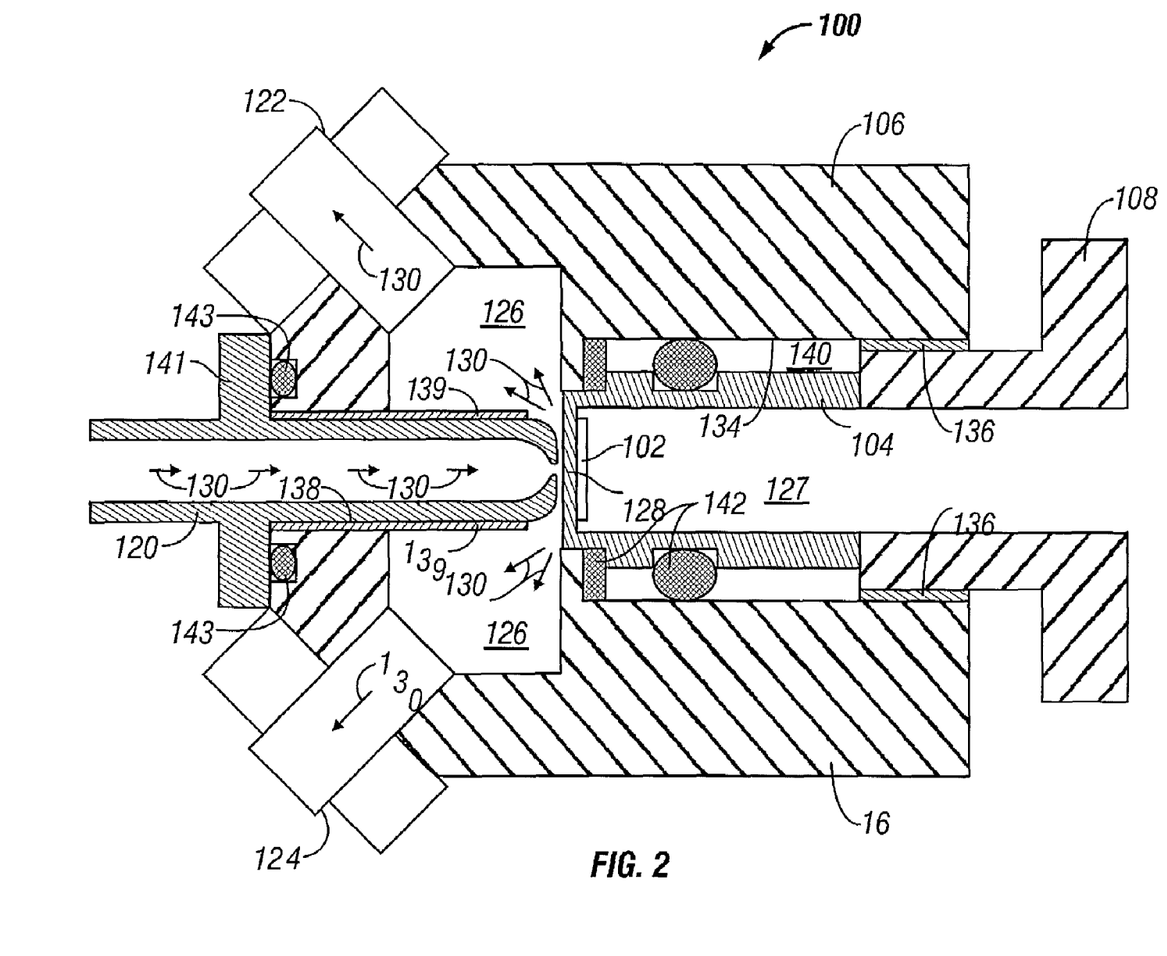
FIG. 2 is a cross-sectional view of a preferred particle sensor according to the principles of the present invention.

In accordance with the principles of the present invention, particle-containing fluid is monitored within a conduit using particle sensor 20. The fluid may comprise a gas such as air or a viscous fluid such and oil or water. Referring to FIG. 2, according to a preferred embodiment of the invention, the particle sensor comprises a monitoring flow cell 100 comprising sensor 102 that produces an output signal in response to the momentum of particles (or contaminants) entrained in a fluid flow impinging on the sensor. Flow cell 100 comprises sensor 102, sensor housing 104, mounting block 106, retaining nut 108, nozzle 120, exhaust ports 122, 124 and plenum 126. Sensor housing 104 and retaining nut 108 each include a central aperture that collectively forms cavity 127 behind sensor 102. Cavity 127 preferably is dimensioned to contain the electronics necessary to operate the acoustic particle alarm. Sensor 102 may be coated with a material having an acoustic impedance that is either low or high relative to the acoustic impedance of the sensor element, to acoustically isolate the sensor element from contact with the electronics within cavity 127.

In operation, particle-containing fluid is pumped through nozzle 120 onto a diaphragm 128, which forms a front face of the sensor. Each particle impacting the diaphragm causes a response in an output of the sensor 102. The fluid travels into flow cell 100 via nozzle 120, enters plenum 126, and is drained through exhaust ports 122, 124, as indicated generally by arrows 130. Sensor 102 is mounted within mounting block 106 such that nozzle 120 produces a jet of fluid impacting substantially perpendicularly on front face 128 of sensor 102. The nozzle is sized to match the pump used in the application, to provide the desired flow velocity.

In the illustrated embodiment, a pair of exhaust ports 122, 124 is employed to drain a single large plenum 126. According to other embodiments of the invention, the flow cell may comprise a single exhaust port used in conjunction with a smaller plenum. Plenum 126 and exhaust ports 122, 124 preferably are configured to maintain the fluid flow out of nozzle 120 and past the front face of sensor 102 in a manner that is substantially radially uniform.

Prior to using the flow cell, sensor housing 104 is inserted into mounting block opening 134 in one side of the mounting block such that sensor 102 is disposed adjacent to nozzle 120. Retaining nut 108 is inserted into mounting block opening 134 following the sensor housing 104. Specifically, retaining nut 108 and opening 134 preferably include threads 136, such that the retaining nut may be inserted and screwed into the opening. Retaining nut 108 advantageously maintains the sensor in a predetermined position with respect to nozzle 120 during operation of flow cell 100. Sensor 120 may be easily removed from mounting black 106 (e.g., for replacement) by unscrewing retaining nut 108 and pulling out sensor housing 104.

Nozzle 120 is attached to mounting block 106 within mounting block opening 138, which is disposed substantially coaxially with mounting block opening 134 on the opposite side of the mounting block. Particularly, mounting block opening 138 extends through mounting block 106 into plenum 126. Mounting block opening 138 preferably is provided with threads 139 that extend into plenum 126, such that the threaded nozzle may be inserted and screwed into the opening. Nozzle 120 includes a length 141 of increased diameter that abuts mounting block 106 when the nozzle is properly inserted within mounting block opening 138. A seal 143 such as a conventional O-ring may be provided between length 141 of increased diameter and mounting block 106. According to further embodiments of the invention, nozzle 120 is fixedly attached to mounting block 106 such that the nozzle is non-removable from the mounting block. For example, the mounting block and nozzle may be manufactured as a single structure, such as by injection molding. Alternatively, mounting block 106 and nozzle 120 may be manufactured separately and attached by welding or using a suitable adhesive.

With further reference to FIG. 2, it is desirable to mount sensor 102 to mounting block 106 such that there is a minimal amount of acoustic coupling between the sensor and the mounting block, thereby minimizing the effect that the sensor mounting has in reducing the resonant frequency. Particularly, any acoustic coupling between the sensor and the mounting block will lower the resonant frequency of the particle sensor. Thus, any metal-to-metal contact between sensor housing 104 and mounting block 106, or between retaining nut 108 and mounting block 106, should be located as far from the acoustic sensor element 102 as is practicable. In the illustrated embodiment, a gap 140 is disposed between sensor housing 104 and mounting block 106 such that there is no metal-to-metal contact between these elements. Therefore, the only metal-to-metal contact between sensor housing 104 and mounting block 106 is by way of retaining nut 108, which contacts sensor housing 104 within mounting block opening 134, and contacts mounting block along threads 136.

One or more seals 142 preferably are provided between sensor housing 104 and mounting block 106 to seal sensor housing 104, gap 140 and retaining nut 108 from the fluid while ensuring minimal acoustic coupling between the sensor and the flow cell. By way of example, seals 142 may comprise acoustically soft O-rings having a low acoustic impedance, or other suitable types of seals that prevent metal-to-metal contact between the housing and the block. Gap 140 between sensor housing 104 and mounting block 106 should be as wide as is consistent with an effective seal between sensor housing 104 and mounting block 106.

In accordance with the principles of the invention, fluid flow is established onto diaphragm 128 such that particulate matter within the fluid flow impacts diaphragm 128 rather than flowing with the fluid away from diaphragm. In the embodiment illustrated of FIG. 2, diaphragm 128 comprises a thin metal substrate that is integral to sensor housing 104, wherein fluid flow is directed such that the impact of a particle is substantially perpendicular to diaphragm 128. The impacting particle imparts its momentum onto diaphragm 128 as the particle is deflected, and the sensor converts the momentum into an electrical output signal whose amplitude is monotonic in the momentum of the particle. The sensor may be bonded to the diaphragm to achieve the desired monotonic relationship between a particle impact and a resultant output signal.

The nature and duration of the output signal is dependent on the electromechanical properties of the particular sensor employed that produces an output signal in response to the momentum of the particles.

Sensor 102 preferably comprises a ceramic piezoelectric acoustic transducer for measuring the momentum of the particles as they impact the diaphragm. For example, the sensor may comprise a stainless steel cup housing a ceramic wafer having such as a 0.035-inch thick wafer of Channel Industry's Lead-Zirconate-Titinate (PZT) ceramic that is ⅜ inches in diameter. The ceramic wafer is initially provided with silver electrodes on both major surfaces, wherein the front electrode is connected by way of a silver trace going over the edge of the ceramic. Electrical leads are connected to the electrodes using room-temperature curing silver-loaded epoxy. A coaxial cable with an electrical connector on one end is then soldered to the electrical leads. The PZT ceramic wafer may be cemented to the inside bottom of the cup, for example using cyanoacrylate adhesive. The cup is then filled with non-conducting electrical potting compound with low acoustic impedance, to secure the electrical leads and to exclude moisture from the cup.

After fabrication, the ceramic wafer-was "poled" by being heated in hot oil while an electric potential is maintained across the wafer. Since the wafer is ferroelectric, the poling process aligns the initially randomly oriented ferroelectric domains so that the poled ceramic behaves as if it were a piezoelectric. In other words, if a time-varying stress is applied to the faces of the poled ceramic wafer, then a corresponding time-varying charge is induced on the electrodes. The sensor's output signal preferably is filtered by a band pass amplifier, and then fed to the alarm circuitry. As would be appreciated by those of skill in the art, other types of sensors may be employed to measure particle impacts without departing from the scope of the present invention.

During operation of the acoustic particle alarm, the particle-containing fluid preferably contains a minimal amount of air bubbles and/or suspended particles, which cause unwanted noise. When the amount of air bubbles and/or suspended particles in the flowing fluid is below a predetermined threshold level, the sensor outputs a random signal (or flow noise) predominately caused by fluid turbulence. The amplitude and frequency structure of the flow noise changes as the flow velocity changes.

According to a preferred implementation of the invention, diaphragm 128 acts as a front face of the sensor, whereas the rear face of the sensor is terminated by a backing material that exhibits low acoustic impedance relative to the acoustic impedance of the transducer material. The diaphragm provides strength in resisting the pressure of the particle-containing fluid, and also protects the sensor from corrosion and contamination. When a particle strikes the diaphragm, a stress impulse is imparted on the diaphragm. The resultant strain in the diaphragm transfers the stress impulse to the sensor, which produces an electrical signal. The amplitude of the electrical signal is inversely related to diaphragm thickness. Diaphragm 128 should be as thin as practicable to minimize the diaphragm's effect on the amplitude and frequency response, yet diaphragm 128 must be thick enough to withstand the forces due to the fluid pressure. Therefore, it is desirable to manufacture the diaphragm to be as thin as is consistent with providing adequate strength to resist the fluid pressure.

The sensor's response to a particle impact is a lightly damped sinusoid, wherein the frequency and damping of the sinusoid is determined by the basic characteristics of the sensor and the effects that diaphragm thickness and sensor mounting impedance have in reducing the output signal. Particle impact signals may be isolated from the flow noise using a conventional band pass filter that is tuned to the expected output signal frequency. Such a filter is suitable to pass the signal, but attenuate the noise in bands outside those frequencies occupied by the signal. Since the flow noise amplitude is inversely related to frequency, an increase in the frequency of the damped sinusoid results in an increase in the output signal to noise ratio.

Figure 3:
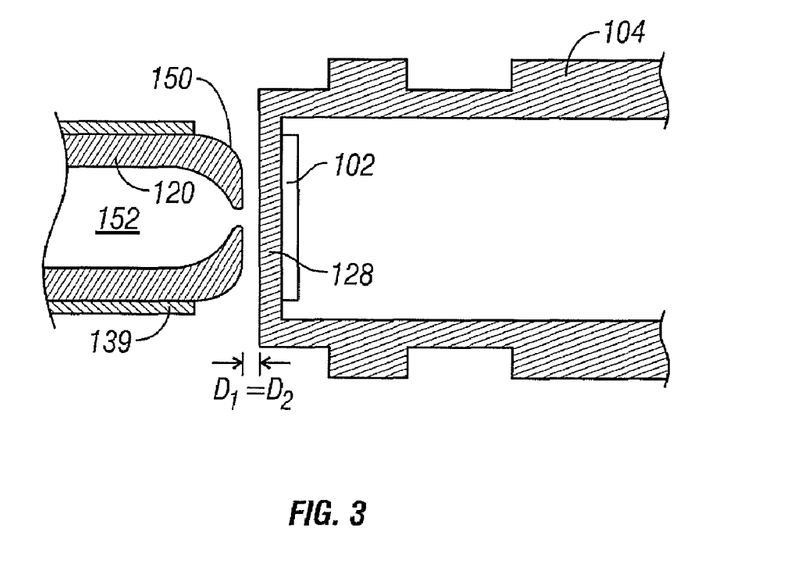
FIG. 3 is a enlarged cross-sectional view of the nozzle, sensor and sensor housing of the preferred particle sensor of FIG. 2.

Referring to FIG. 3, mouth 150 of nozzle 120 is disposed at a predetermined distance $D_1$ from diaphragm 128. Mouth 150 of nozzle 120 preferably includes a substantially conical bore 152 that causes the diameter of the jet of fluid exiting the mouth to decrease to a minimum diameter (the waist) upon exiting mouth 150 and then increase. Distance $D_2$ between the mouth of the nozzle and the waist of the jet is a monotonically increasing function of bore mouth diameter. Predetermined distance $D_1$ between mouth 150 and diaphragm 128 should be selected such that $D_1$ approximately equals $D_2$, wherein the waist is substantially disposed at the diaphragm, thereby maximizing the concentration of particles impacting sensor 102. However, in order to prevent the largest particles from being caught between mouth 150 and diaphragm 128, predetermined distance $D_1$ should be greater than the maximum dimension of the largest particle to be passed. If the maximum dimension of the largest particle is greater than $D_2$, then predetermined distance $D_1$ should be selected to be large enough to permit the largest particles to pass, with a consequent reduction in the concentration of particles impacting diaphragm 128.

In order to prevent clogging of nozzle bore 152, the minimum inside diameter of the bore must be greater than the maximum dimension of the largest particle. By way of example, if the largest particle has a maximum dimension of 100 microns, a suitable minimum diameter for nozzle bore 152 is 150 microns. According to the principles of the present invention, nozzle bore 152 is substantially conical in order to concentrate the jet by forming a waist after it leaves the nozzle. By contrast, with a cylindrical bore, the jet begins to expand as soon as the fluid exits the nozzle. According to some embodiments, nozzle bore taper may be determined based upon factors such as the viscosity, density and flow velocity of the particle-containing fluid to be passed through nozzle 120.

The flow of particle-containing fluid through the nozzle preferably is laminar rather than turbulent. If the flow is turbulent, a particle's impact on the diaphragm is less likely to be substantially perpendicular to the diaphragm, and therefore result in less than optimal momentum transfer. Moreover, the flow noise induced in the sensor is greater for turbulent flow than for laminar flow. For these reasons, fluid flow preferably is maintained in the laminar range during operation of the flow cell.

Flow velocity is an additional factor to consider when operating the flow cell. An increase in flow velocity causes an increase in particle momentum transfer that produces a proportional increase in signal amplitude. However, flow noise also increases as the flow velocity is increased. A preferred flow velocity is therefore set at a maximum level without raising the flow noise into an intolerable flow noise range. The preferred flow velocity typically falls just below the velocity at which fluid flow becomes turbulent.

Flow noise decreases with increasing signal frequency. The sensor's output signal preferably is generated at a high enough frequency so that the flow noise is relatively low. The signal is then passed through a band pass filter that passes the signal, but attenuates the noise in bands outside those frequencies occupied by the signal. The electronic circuitry used to process the signal from the transducer has inherent internal noise. According to some embodiment of the invention, flow velocity is increased to a point at which flow noise begins to add to the overall noise level. At this velocity, the level of flow noise (in the absence of contamination) is approximately equal to the level of the amplifier noise, and the output signal is monotonic in the mass of the particle impacting the sensor. If the particle is substantially spherical, the output signal will be proportional to the cube of the particle's diameter.

According to another aspect of the invention, the concentration of the particles entrained in the fluid is determined in numbers per unit volume of fluid and an alarm is provided to indicate when the signal amplitude exceeds a predetermined threshold. Particle concentration may be presented as a number or, alternatively, may be used to indicate the concentration in excess of a specified threshold concentration for particles or particle-like objects of a specified or larger size. Electronic circuitry processes the signal from the sensor such that if the signal amplitude exceeds a preset predetermined, a pulse is passed on to an accumulator circuit. When the accumulated number of pulses exceeds another predetermined threshold, an output is provided to ring an alarm or to activate a light or a series of lights, wherein each light in sequence corresponds to a larger accumulation of pulses and hence a greater particle concentration. As would be appreciated by those of ordinary skill in the art, other types of alarms and indicators may be employed without departing from the scope of the present invention.

Momentum is a directed vector quantity: $\bar{p}=m\bar{v}$ where $\bar{p}$ is the momentum, m is the mass of the particle and $\bar{v}$ is its vector velocity. Signal amplitude provides an indication of the particle size via the particle momentum because of the following factors: (1) the output signal amplitude is general a monotonic function of the particle momentum; (2) the magnitude of the momentum is equal to the product of particle mass and speed; and (3) particle mass is related to particle size.

When a particle impacts on the face of the sensor's diaphragm, its direction of motion changes so it can follow the flow out of the unit. This change of direction is accompanied by a change in the particle's momentum. Of course, it is a fundamental principle of physics that momentum is conserved such that if a particle had a velocity $\bar{v}_{bi}$ before impact and a velocity $\bar{v}_{ai}$ after impact, then it had momentum $\bar{p}_{bi}=m\bar{v}_{bi}$ before impact and momentum $\bar{p}_{ai}=m\bar{v}_{ai}$ after impact. Since the sensor diaphragm had approximately zero momentum before the impact, the particle-diaphragm system had the momentum of the particle before impact, such that $\bar{p}_{pd}=\bar{p}_{bi}=m\bar{v}_{bi}$, where $\bar{p}_{pd}$ is the momentum of the particle-diaphragm system. By conservation of momentum, the system must have the same momentum after impact so that the after impact diaphragm momentum, $\bar{p}_d$ plus the after impact particle momentum, $\bar{p}_{ai}$, must equal the conserved particle-diaphragm system momentum, $\bar{p}_{pd}$, which is equal to the before impact particle momentum, $\bar{p}_{bi}$. Therefore, the following equations are obtained:

$$\bar{p}_d+\bar{p}_{ai}=\bar{p}_{bi} \quad (0.1)$$

or $$\bar{p}_d=\bar{p}_{bi}-\bar{p}_{ai}=m(\bar{v}_{bi}-\bar{v}_{ai}). \quad (0.2)$$

If the particle's impact is normal to the diaphragm surface and it rebounds reversing its direction with the same speed that it had before impact and with its velocity vector in the opposite direction, the particle has a momentum of the same magnitude in the opposite direction. If the particle rebounds with the same speed as its impact speed, the particle and diaphragm are said to have a unity coefficient of restitution. In this case, $\bar{v}_{ai}=-\bar{v}_{bi}$, and according to Equation (0.2), the diaphragm's momentum after impact is twice the particle momentum before impact such that:

$$\bar{p}_d=2m\bar{v}_{bi}=2\bar{p}_{bi} \quad (0.3)$$

Momentum is imparted to the diaphragm as an impulse of force that stimulates the sensor (comprising the diaphragm and attached piezoelectric element) to ring in a manner characteristic of the transducer assembly. The piezoelectric element converts the mechanical ringing into a corresponding electrical signal. The amplitude and detailed ringing of the sensor's output signal depends on the magnitude and direction of the momentum transfer to the diaphragm and the location on the diaphragm where the transfer occurred. Maximum momentum transfer is achieved when a particle has an impact normal to the sensor's diaphragm and a rebound speed equal to the impact speed (i.e., unity coefficient of restitution). It follows axiomatically that the maximum momentum transfer condition results in the maximum electrical signal. In view of the above, it is a goal of the implementation of the transducer assembly to arrange for the particles to impact the sensor diaphragm at a substantially normal angle of incidence. In reality, there may be a number of deviations from this ideal impact. For example, the impact may not be normal to the diaphragm's surface or the rebound coefficient of restitution may be less than unity so that the rebound speed is less than the impact speed.

The disclosed embodiments of the present invention involve determining the concentration of solid particles in a fluid. According to further embodiments of the invention, the concentration of small "blobs" of disparate fluid may also be indicated. By way of example, small bubbles of air entrained in the fluid can be detected and the concentration indicated.

Additionally, small "blobs" of water in oil can be detected and the concentration indicated.

Figure 4:
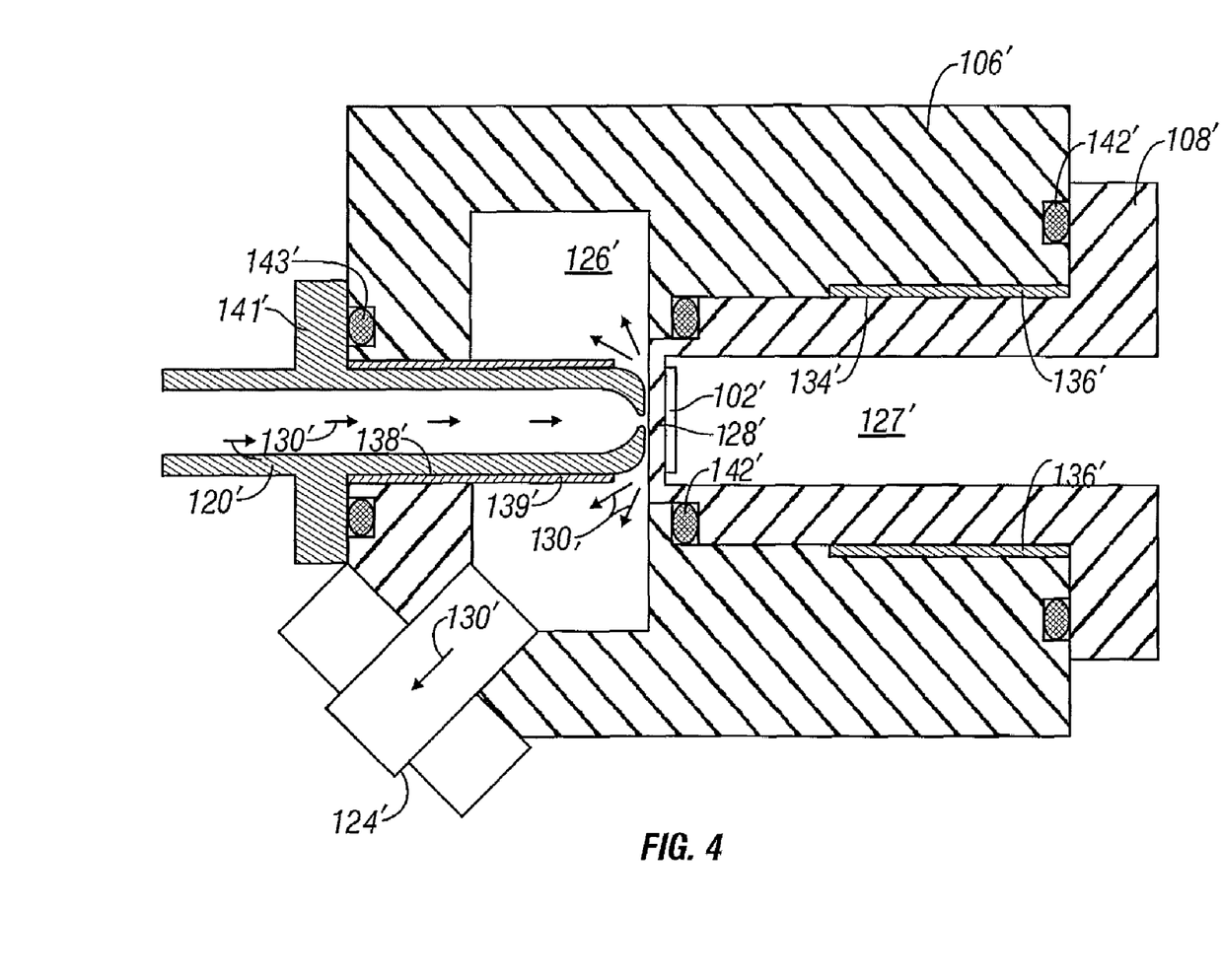
FIG. 4 is a cross-sectional view of an alternative particle sensor according to the principles of the present invention.

Referring to FIG. 4, an alternative particle sensor of the present invention comprises a monitoring flow cell 100' comprising sensor 102', mounting block 106', integral sensor housing and retaining nut 108', nozzle 120', exhaust port 124' and plenum 126'. Integral sensor housing and retaining nut 108' includes a central aperture forming cavity 127' behind sensor 102'. A gap 140' is provided between integral sensor housing and retaining nut 108' and mounting block 106' such there is limited metal-to-metal contact between these components. Gap 140' should be as wide as is consistent with an effective seal between integral sensor housing and retaining nut 108' and mounting block 106'.

Similar to the previous particle sensor embodiment, particle-containing fluid is pumped through nozzle 120' onto diaphragm 128', such that each particle impacting the diaphragm causes a response in the sensor's output. The fluid travels into flow cell 100' via nozzle 120', enters plenum 126', and is drained through exhaust port 124', as indicated generally by arrows 130'. Sensor 102' is mounted within mounting block 106' such that nozzle 120' produces a jet of fluid impacting substantially perpendicularly on front face 128' of sensor 102'. Plenum 126' and exhaust port 124' preferably are configured to maintain the fluid flow out of nozzle 120' and past the front face of sensor 102' in a manner that is substantially radially uniform.

Prior to using the flow cell, integral sensor housing and retaining nut 108' is inserted into mounting block opening 134' in one side of the mounting block such that sensor 102' is disposed adjacent to nozzle 120'. Integral sensor housing and retaining nut 108' and opening 134' preferably include threads 136', such that the retaining nut may be inserted and screwed into the opening. Integral sensor housing and retaining nut 108' advantageously maintains the sensor in a predetermined position with respect to nozzle 120' during operation of flow cell 100'. Sensor 120' may be easily removed from mounting black 106' (e.g., for replacement) by unscrewing and pulling out the integral sensor housing and retaining nut.

Nozzle 120' is attached to mounting block 106' within mounting block opening 138', which is disposed substantially coaxial to mounting block opening 134' on the opposite side of the mounting block. Mounting block opening 138' is provided with threads 139' that extend into plenum 126', such that the threaded nozzle may be inserted and screwed into the opening. Nozzle 120' includes a length 141' of increased diameter that abuts mounting block 106' when the nozzle is properly inserted within mounting block opening 138'. A seal 143' may be provided between length 141' of increased diameter and mounting block 106'. In addition, one or more seals 142' may be provided between integral sensor housing and retaining nut 108' and mounting block 106' to seal integral sensor housing and retaining nut 108' from the fluid and to ensure minimal acoustic coupling between the sensor and the flow cell. By way of example, seals 142', 143' may comprise O-rings having a low acoustic impedance, or other suitable types of seals that provide a fluid seal between the housing and the block. According to additional embodiments of the invention, nozzle 120' may be fixedly attached to mounting block 106' such that the nozzle is non-removable from the mounting block. For example, mounting block 106' and nozzle 120' may be manufactured as a single structure, such as by injection molding, or these components may be manufactured separately and then attached by welding or using a suitable adhesive.

Thus, it is seen that an acoustic particle alarm having a particle sensor is provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

What is claimed is:

1. An acoustic particle alarm, comprising:
   a mounting block;
   a particle sensor, disposed in a sensor housing releasably attached to the mounting block, for detecting when particles entrained in a fluid flow impinging on a front face of the sensor exceeds a specified size or concentration; and
   a nozzle, releasably attached to the mounting block opposite the particle sensor, for directing the fluid flow such that the particles impact the sensor in a direction substantially normal to the front face of the sensor.

2. The acoustic particle alarm of claim 1, wherein each particle impacting the front face of the sensor causes an electrical response in the output of the sensor that is monotonic in the momentum of the impinging particle.

3. The acoustic particle alarm of claim 1, further comprising an indicator for indicating when the integrated particle impacts are greater than a predetermined threshold level.

4. The acoustic particle alarm of claim 1, wherein:
   the nozzle is releasably attached to the mounting block within a first threaded mounting block opening in one side of the mounting block;
   the sensor housing is inserted in a second threaded mounting block opening on the opposite side of the mounting block; and
   the sensor housing is secured within the mounting block opening using a retaining nut that is releasably attached within the second threaded mounting block opening.

5. The acoustic particle alarm of claim 4, wherein the sensor housing and retaining nut each include a central aperture that forms a cavity adjacent to the sensor, wherein the cavity is dimensioned to contain electronics for operating the acoustic particle alarm.

6. The acoustic particle alarm of claim 1, wherein:
   the nozzle is releasably attached to the mounting block within a first threaded mounting block opening in one side of the mounting block; and
   the sensor is housed within an integrated sensor housing and retaining nut that is attached to the mounting block within a second threaded mounting block opening on the opposite side of the mounting block.

7. The acoustic particle alarm of claim 6, wherein the integrated sensor housing and retaining nut includes a central aperture that forms a cavity adjacent to the sensor, wherein the cavity is dimensioned to contain electronics for operating the acoustic particle alarm.

8. The acoustic particle alarm of claim 1, wherein the sensor comprises a ceramic piezoelectric acoustic transducer that produces an electric output signal in response to the particles as they impact the diaphragm.

9. The acoustic particle alarm of claim 1, further comprising a plenum and at least one exhaust port that are configured to maintain fluid flow out of the nozzle such that the fluid flow impinges on the front face of the sensor and is deflected into the plenum in a manner that is substantially radically uniform.

10. The acoustic particle alarm of claim 1, wherein the front face comprises a thin metal substrate that provides strength in resisting the fluid pressure and protects the sensor from corrosion and contamination.

11. An acoustic particle alarm, comprising:
    a mounting block including a sensor housing;
    a particle sensor that provides an electric output signal in response to particles entrained in a fluid flow impinging on a diaphragm of the sensor, wherein the sensor is disposed within the sensor housing; and
    a nozzle for directing the fluid flow such that a jet of fluid exiting a mouth of the nozzle forms a waist that is located substantially at the diaphragm.

12. The acoustic particle alarm of claim 11, wherein the particles impact the sensor in a direction substantially normal to the diaphragm.

13. The acoustic particle alarm of claim 11, further comprising a gap that is disposed between the sensor housing and the mounting block to reduce the amount of acoustic coupling between the sensor and the mounting block.

14. The acoustic particle alarm of claim 11, further comprising one or more seals that are provided between the sensor housing and the mounting block to prevent fluid from leaking past the sensor housing, said seals being made of acoustically soft material to reduce the amount of acoustic coupling between the sensor and the mounting block.

15. The acoustic particle alarm of claim 11, wherein:
    the nozzle includes a mouth that is disposed at a predetermined distance from the diaphragm;
    the mouth of the nozzle includes a substantially conical bore that causes the fluid exiting the mouth to form a waist; and the predetermined distance is selected such that the waist is substantially disposed at the diaphragm, thereby maximizing the concentration of particles impacting the sensor.

16. The acoustic particle alarm of claim 15, wherein:

the predetermined distance is selected to be greater than a maximum dimension of the largest particle to be passed; and a minimum inside diameter of the substantially conical bore is greater than the maximum dimension of the largest particle to be passed.

17. The acoustic particle alarm of claim 11, wherein the flow velocity of the fluid through the nozzle is selected to be just below the velocity at which fluid flow becomes turbulent.

* * * * *